US011510719B2

(12) United States Patent
Défossez et al.

(10) Patent No.: US 11,510,719 B2
(45) Date of Patent: Nov. 29, 2022

(54) INTRAMEDULLARY NAIL RETAINING ENDCAPS

(71) Applicant: DEPUY SYNTHES PRODUCTS, INC., Raynham, MA (US)

(72) Inventors: Henri Défossez, Neuchatel (CH); Gregor Spreiter, Solothurn (CH); Simon Scherrer, Zurich (CH); Simon Wampfler, Lohn-Ammannsegg (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 512 days.

(21) Appl. No.: 16/562,272

(22) Filed: Sep. 5, 2019

(65) Prior Publication Data

US 2021/0068880 A1    Mar. 11, 2021

(51) Int. Cl.
*A61B 17/88* (2006.01)
*A61B 17/74* (2006.01)
*A61B 17/00* (2006.01)

(52) U.S. Cl.
CPC .......... *A61B 17/8872* (2013.01); *A61B 17/74* (2013.01); *A61B 17/8897* (2013.01); *A61B 2017/00477* (2013.01); *A61B 2017/00862* (2013.01); *A61B 2017/00867* (2013.01)

(58) Field of Classification Search
CPC ... A61B 17/72; A61B 17/7233; A61B 17/725; A61B 17/8872; A61B 17/74; A61B 17/8897; A61B 17/84; A61B 17/1717; A61B 17/1725; A61B 17/744; A61B 2017/00477; A61B 2017/00862; A61B 2017/00867

USPC ........................................... 606/62, 300–321
See application file for complete search history.

(56) References Cited

U.S. PATENT DOCUMENTS

| | | | |
|---|---|---|---|
| 9,237,949 B2 * | 1/2016 | Podolsky | A61B 17/164 |
| 9,532,814 B2 * | 1/2017 | Harper | A61B 17/7085 |
| 2003/0074000 A1 * | 4/2003 | Roth | A61B 17/744 |
| | | | 606/62 |
| 2003/0074003 A1 | 4/2003 | Deslauriers et al. | |
| 2005/0216015 A1 * | 9/2005 | Kreidler | B25B 23/106 |
| | | | 606/104 |
| 2008/0255576 A1 * | 10/2008 | Protopsaltis | A61B 17/7091 |
| | | | 227/176.1 |
| 2009/0187194 A1 * | 7/2009 | Hamada | A61B 17/7001 |
| | | | 606/104 |
| 2010/0069969 A1 * | 3/2010 | Ampuero | A61B 50/30 |
| | | | 606/301 |
| 2010/0331897 A1 * | 12/2010 | Lindner | A61B 17/7041 |
| | | | 606/305 |

(Continued)

FOREIGN PATENT DOCUMENTS

WO    2016/000784 A1    1/2016

*Primary Examiner* — Jessica Weiss
(74) *Attorney, Agent, or Firm* — Fay Kaplun & Marcin, LLP

(57) ABSTRACT

An endcap for engaging a proximal end of an intramedullary nail. The endcap includes a body extending from a first end to a second end and configured to engage a channel of an intramedullary nail. The endcap also includes a head portion at the first end of the body. The head portion includes a recess sized and shaped to receive a driving element of a drive shaft. The recess includes elastic tabs extending radially toward a central axis of the recess to engage and retain a driving element received therein.

19 Claims, 2 Drawing Sheets

(56) References Cited

U.S. PATENT DOCUMENTS

| | | | |
|---|---|---|---|
| 2012/0226326 A1* | 9/2012 | Overes | A61B 17/1739 |
| | | | 606/329 |
| 2013/0144345 A1 | 6/2013 | Felder et al. | |
| 2015/0250515 A1* | 9/2015 | Terrill | A61B 17/8685 |
| | | | 606/306 |
| 2016/0317200 A1* | 11/2016 | Hoogervorst | A61B 17/921 |
| 2020/0323568 A1* | 10/2020 | Daly | A61B 17/7233 |
| 2020/0330137 A1* | 10/2020 | Rezach | A61B 17/7091 |
| 2021/0077172 A1* | 3/2021 | Défossez | A61B 17/8897 |
| 2021/0346075 A1* | 11/2021 | Daly | A61B 17/8872 |

* cited by examiner

INTRAMEDULLARY NAIL RETAINING ENDCAPS

FIELD OF INVENTION

The present invention relates generally to a system for fixation of two or more parts of a fractured bone. More specifically, the present invention relates to an endcap and intramedullary nail for internal fixation for a long bone, such as a femur.

BACKGROUND

Fractures of the femur often occur in the femoral neck and intertrochanteric regions. Such fractures may be treated with screws or other fixation devices inserted into or through a bone to stabilize and fix the positioning of different portions of the bone relative to one another after they have been placed into corrective alignment. Trochanteric bone fixation treatments often comprise the insertion of an intramedullary nail into a medullary cavity of a bone and the subsequent insertion of a bone fixation nail into a condylar portion of the bone at an angle relative to the intramedullary nail (i.e., along an axis of the trochanter).

SUMMARY OF THE INVENTION

One exemplary embodiment of the present invention is directed to an endcap for engaging a proximal end of an intramedullary nail. The endcap comprises a body extending from a first end to a second end and configured to engage a channel of an intramedullary nail. The endcap also comprises a head portion at the first end of the body. The head portion includes a recess sized and shaped to receive a driving element of a drive shaft. The recess includes elastic tabs extending radially toward a central axis of the recess to engage and retain a driving element received therein.

In another aspect of the present application, a system for engaging a proximal end of an intramedullary nail is provided. The system comprises a tool comprising a drive shaft having a driving element. The system also comprises an endcap comprising a body extending from a first end to a second end and configured to engage a channel of an intramedullary nail, and a head portion at the first end of the body. The head portion including a recess sized and shaped to receive the driving element of the drive shaft. The recess including elastic tabs extending radially toward a central axis of the recess to engage and retain the driving element therein.

These and other aspects of the invention will become apparent to those skilled in the art after a reading of the following detailed description of the invention, including the figures and appended claims.

DETAILED DESCRIPTION

Figure 1:
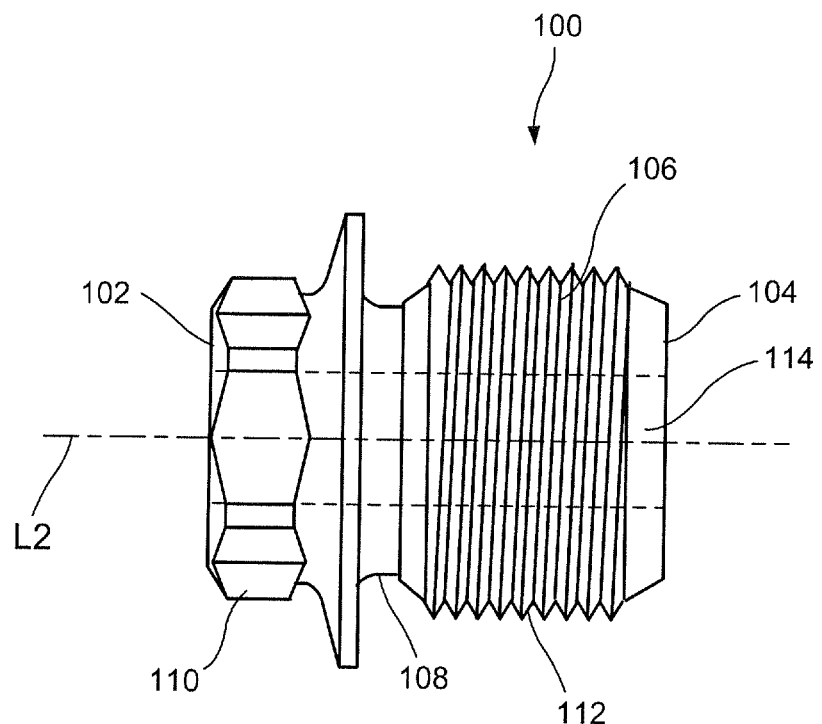
FIG. 1 show a side view of an endcap according to an embodiment of the present invention.

The present disclosure may be further understood with reference to the following description and the appended drawings, wherein like elements are referred to with the same reference numerals. It should be noted that the terms "proximal" and "distal," as used herein are intended to refer to a direction toward (proximal) and away from (distal) a user of the device.

FIGS. 1-4 show an endcap 100 couplable to a proximal end 12 of an intramedullary nail 10. In particular, the endcap 100 is configured to be inserted into a proximal opening 14 of a channel 16 in the intramedullary nail 10 to close the proximal opening 14 of the channel 16 to prevent bone ingrowth into the channel 16. The endcap 100 is configured to reversibly engage and/or disengage with an interior surface of the channel 16 in the intramedullary nail 10 via any suitable engagement structure, such as, for example, threading 112 configured to engage corresponding threading within the interior surface of the channel. The endcap 100 extends from a proximal end 102 to a distal end 104 and includes a body portion 106 and a head portion 110 proximal of the body portion 106. The body portion 106 extends from a proximal end 108 thereof to the distal end 104 of the endcap 100. The head portion 110 extends proximally from to the proximal end 108 of the body portion 106. In some embodiments, the endcap 100 includes a lumen 114 extending from the proximal end 102 to the distal end 104 along a longitudinal axis 116 thereof. The lumen 114 being configured to receive a guide wire 18 therethrough.

Figure 2A:
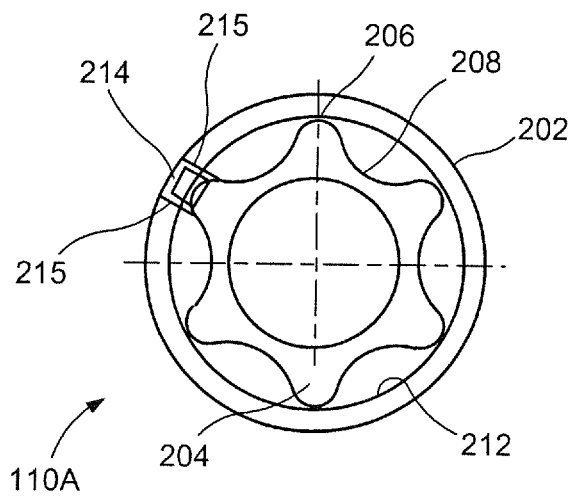
FIG. 2a shows a top view of an endcap according to an embodiment of the present invention.

The head portion 110 discussed above and shown in FIGS. 1 and 3 may encompass various embodiments, such as for example, the two different exemplary embodiments of a head portion 110a, 110b shown in FIGS. 2a and 2b and discussed further below. As shown in FIG. 2a, the head portion 110a of the endcap has a retaining wall 202 around a circumference of the head portion 110a, and defining a recess 204 therein for engaging a tool 300, such as, for example, a driving element 302 of a drive shaft 304. The recess 204 is suitably sized and shaped to securely engage the driving element 302 so that manipulation of the driving shaft 304 does not accidentally disengage the head portion 110a from the driving element 302. This minimizes the risk that the endcap 100 will be accidentally dropped during implantation and thereby reducing the risk of delays during surgery caused by lost of endcaps either within the body of the patient or elsewhere within the surgical room. In particular, the recess 204 is suitably sized and shaped to securely engage the driving element 302 so that manipulation of the driving shaft 304 while the tool 300 is engaged with the recess 204 drives the endcap 100 into the channel 16 of the intramedullary nail 10. More particularly, the recess 204 is configured to securely engage the driving element 302 such that rotation of the driving shaft 304 transfers torque from the driving shaft 304 through the head portion 110 to drive the body portion 106 of the endcap 100 into the channel 16. In one example, the recess 204 is suitably sized and shaped by milling the head portion 110a to create the recess 204 in a desired size and shape.

In one embodiment, the driving element 302 has a substantially polygonal cross-section, for example, a cross-section that is substantially hexagonal in a plane orthogonal to a longitudinal axis L1 of the driving shaft 304. In the embodiment shown in FIG. 3, the driving element 302 is tapered at its proximal and distal ends 308, 306. The driving element 302 shown in FIG. 3 has a bulbous shape where a cross-sectional diameter of the driving element 302 is the largest at the midpoint 310 between the proximal and distal ends 308, 306. The driving element 302 shown in FIG. 3 tapers from the midpoint 310 to a narrower proximal end 308, and also tapers from the midpoint 310 to a narrower distal end 306 to form a concave exterior shape permitting the driving element 302 to remain engaged with the recess 204 even if the longitudinal axis L1 of the driving shaft 304 is mis-aligned with the axis 116 of the end cap 100.

The recess 204 has a size and shape corresponding to that of the driving element 302 for receiving and securely engaging the driving element 302. In particular, the recess 204 has a shape that is correspondingly polygonal (i.e., the recess 204 has a cross-section that is substantially the same polygon as the cross-section of the driving element 302). More particularly, the recess 204 has a substantially hexagonal cross-section when the driving element 302 is a hex-key or other driving element having a substantially hexagonal shape. The recess 204 includes a plurality of peaks 206 corresponding to each of the vertices of the polygonal shape. Each of the peaks 206 has a convex shape extending radially from the longitudinal axis 116 towards an interior surface 212 of the retaining wall 202.

In the embodiment for a head portion 110a shown in FIG. 2a, at least one of the peaks 206 may further include a first elastic tab 214 extending from the retaining wall 202 radially towards the longitudinal axis 116 which deforms to move radially outward from a relaxed configuration to receive the driving element 302 in the recess 204. The first elastic tab 214 is biased toward the relaxed configuration such that when the midpoint 310 of the driving element 302 is inserted distally past the first elastic tab 214, the bias of the first elastic tab 214 urges the first elastic tab 214 radially inward toward the longitudinal axis L2, The bias of the first elastic tab 214 pushes against an exterior surface the driving element 302 as it is further inserted into the recess and expands radially inward toward the longitudinal axis L2 to locking engage the driving element 302 at its proximal end 308.

The first elastic tab 214 reversibly deforms to allow the entire length of the driving element 302 (including the midpoint 310 where the driving element 302 is the widest) to be inserted therepast and subsequently lockingly engage the tool 300 at the proximal end 308 of the driving element 302 where it tapers to a connection with the distal end 314 of the driving shaft 304 and thereby forming a groove for longitudinally interlocking with the first elastic tab 214 when it is in a relaxed configuration. The bias of the first elastic tab 214 pushes radially inward to provide a resistance against removal of the driving element 302 from the recess 204. The resistance may be overcome by application of a predetermined level of force to overcome the bias of the first elastic tab 214 and compress or push radially outwardly the first elastic tab 214 as the driving element 302 is retracted proximally from the recess 204.

In one example, the first elastic tab 214 is formed by longitudinal slotted cuts 215 within the retaining wall 202 and irreversibly pushing (e.g., plastically deforming) a portion of the retaining wall 202 between the slotted cuts 215 radially inward toward the longitudinal axis to form the first elastic tab 214. The first elastic tab 214 may be in a relaxed configuration when the driving element 302 is outside of the recess 204 and deforms (e.g., may be compressed or pushed radially outwardly) as the driving element 302 is inserted into the recess 204. The first elastic tab 214 is biased towards the relaxed configuration such that when the driving element 302 is inserted into the recess 204, the bias urges the first elastic tab 214 radially inward toward the longitudinal axis against an external surface of the driving element 302 and to frictionally engage the external surface of the driving element 302. The recess 204 also includes a plurality of indentations 208 positioned between the peaks 206 each having a concave shape facing the interior surface 212 of the retaining wall 202.

Figure 2B:
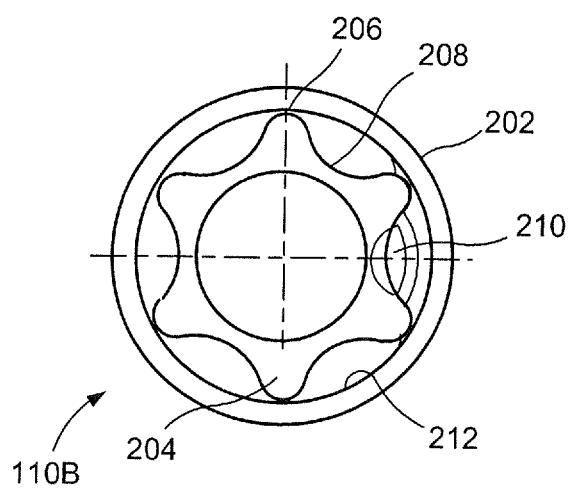
FIG. 2b shows a top view of an endcap according to an alternative embodiment of the present invention.
Figure 3:
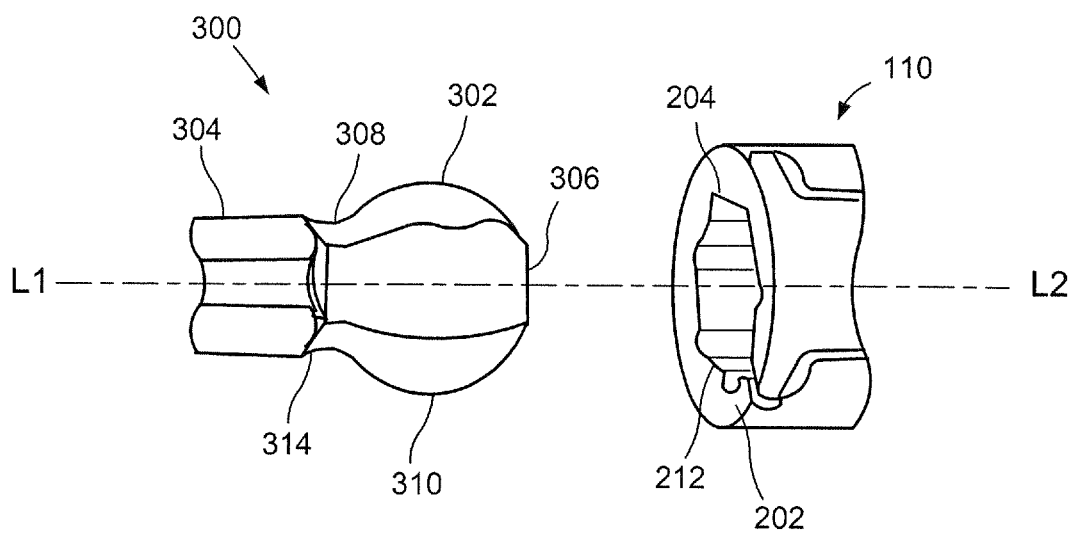
FIG. 3 shows a perspective view of the endcap of FIG. 1 along with a tool for reversibly engaging and driving the endcap into a channel of an intramedullary nail.

The head portion 110a shown in FIG. 2b is substantially similar to the head portion 110b of FIG. 2a, where like elements are referenced with like reference numerals. FIG. 2b shows a head portion 110b having a second elastic tab 210 formed in at least one of the indentations 208. The second elastic tab 210 is included in this embodiment in place of the first elastic tab 214 described above in the embodiment shown in FIG. 2a. It is noted that the head portion 110 of the endcap 100 may include one or more of either the first elastic tab 214 or the second elastic tab 210, however, the first elastic tab 214 and the second elastic tab 210 are not both incorporated into a single embodiment. The second tab 210 extends radially inward from the longitudinal axis 116 and configured to be pushed radially outward from a relaxed configuration to receive the driving element 302 in the recess 204. The second elastic tab 210 is also biased toward the relaxed configuration to provide a resistance against removal of the driving element 302 from the recess 204, in a similar manner as describe above with respect to the first elastic tab 214. In particular, the second elastic tab 210 also reversibly deforms to allow the entire length of the driving element 302 to be inserted therepast and lockingly engage the tool 300 at the connection between the proximal end 308 of the driving element 302 and the distal end 314 of the driving shaft 304.

The first elastic tab 214 or second elastic tab 210 may be unitarily formed as part of the head portion 110 of the endcap 100, or may be a separate component that is attached to the interior surface 212 of the retaining wall 202 of the recess portion 204 of the endcap 100. The first elastic tab 214 or second elastic tab 210 may be formed from any suitable elastic material that deforms when an external force is applied to the elastic material and resumes its original shape once the external force is removed. In one embodiment, the elastic material may be a memory metal alloy, for example, nitinol, Ti-6Al-7Nb (TAN) and/or Ti-6Al-4V (TAV). In particular, the elastic material may consist of a nickel-titanium alloy, in which 45%<Ni<55%, 45% Ti<55% and x+y=100%. Such a material may be particularly biocompatible and highly elastic. The memory metal alloy may have a transition temperature of more than about 50° C. and, more preferably, more than about 80° C. In another embodiment, the transition temperature may be more than about 100° C. and, preferably, more than about 120° C. The first elastic tab 214 or second elastic tab 210 may be pre-shaped in the relaxed configuration extending from the retaining wall 202 into the recess 204 of the head portion 110 of the endcap 100.

The body portion 106 of the endcap 100 is configured to be inserted into and engage a channel 16 of an intramedullary nail 10. In particular, the distal end 104 is suitably sized and shaped to be inserted into a proximal opening 14 of a channel 16 in the intramedullary nail 10 and fixedly engage an interior of the channel 16 of the intramedullary nail 10. The body portion 106 may include any suitable engagement structure, e.g., threading 112, snap fasteners, adhesives or screws to attach endcap 100 to the channel of the intramedullary nail. In some embodiments, the body portion 106 may include at least a portion having a threading 112 configured to threadedly engage the interior of the channel 16 of the intramedullary nail 10. The threading 112 may extend along a part of or an entire longitudinal length of the body portion 106. The threading 112 is configured to mate with corresponding threading located in the interior of the channel 16 of the intramedullary nail 10 as the endcap 100 is driven into the channel 16 of the intramedullary nail 10, to secure the endcap 100 at the proximal end 12 of the intramedullary nail 10.

Figure 4:
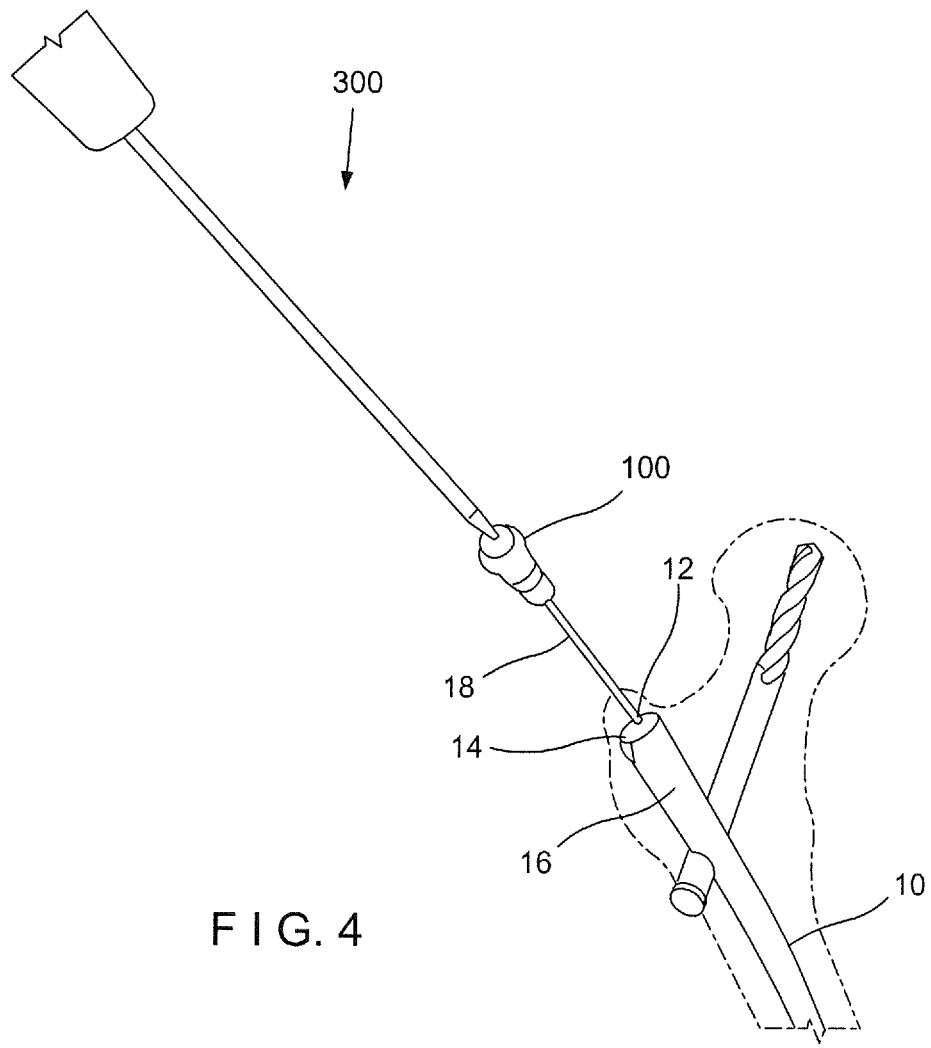
FIG. 4 shows a perspective view a system for of a femur including an intramedullary nail and the endcap of FIG. 1 being guided over a guide wire for insertion into a proximal opening of a channel of an intramedullary nail.

As can be seen in exemplary embodiment shown in FIG. 4, the endcap 100 may be installed at the proximal end 12 of the intramedullary nail 10 by inserting a guidewire 18 into the channel 16 of the intramedullary nail 10 and sliding the endcap 100 over the guidewire 18 via lumen 114 towards a desired position over the proximal end 12 of the intramedullary nail 10. Specifically, the endcap 100 is inserted into the channel 16 of the intramedullary nail 10 to prevent bone ingrowth into the channel 16 such that a removal instrument (not shown) can be easily mounted onto the proximal end 140 of the channel 16 without tissue obstruction after the intramedullary nail 10 has been implanted and allowed to remain within the bone for a period of time to allow the bone to heal. The tool 300 may also be configured to receive the guidewire 18 therethrough and slide into position to engage the head portion 110 of the endcap 100. Once the tool 300 has been inserted into the recess 204 of the endcap 100, it is quickly and securely engaged to the head portion 110 such that manipulation of the tool 300 translates applied forces and/or torque to the endcap 100. In particular, the tool 300 may be manipulated to drive the body portion 106 into the channel 16 of the intramedullary nail 10. The endcap 100 may be driven into the channel 16 of the intramedullary nail 10 such that a portion of or an entire longitudinal length of the body portion 106 of the endcap 100 lies within the channel 16 when it is fully inserted. In some embodiments, only a portion of the length of the body portion 106 is inserted and engaged with the channel 16 such that the endcap 100 provides a proximal extension to the intramedullary nail 10. The proximal extension may provide additional stability and/or structural support to the bone.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. An endcap for engaging a proximal end of an intramedullary nail, comprising:
    a body extending from a first end to a second end and configured to engage a channel of an intramedullary nail; and
    a head portion at the first end of the body, the head portion including a recess sized and shaped to receive a driving element of a drive shaft, the recess including elastic tabs biased to extend radially toward a central axis of the recess to engage and retain the driving element received therein.

2. The endcap of claim 1, wherein the body comprises threading to threadedly engage the channel of the intramedullary nail.

3. The endcap of claim 1, wherein the elastic tabs are formed from an elastic material.

4. The endcap of claim 3, wherein the elastic material is a biocompatible memory metal alloy.

5. The endcap of claim 3, wherein the elastic material is selected from the group consisting of nitinol, Ti-6Al-7Nb (TAN), and Ti-6Al-4V (TAV).

6. The endcap of claim 1, wherein the elastic tabs are configured to move from a relaxed configuration in which the elastic tabs extend radially toward the central axis to a compressed configuration in which the elastic tabs are pushed radially outward from the central axis.

7. The endcap of claim 6, wherein the elastic tabs are biased toward the relaxed configuration.

8. The endcap of claim 7, wherein the elastic tabs are biased to provide a resistance against removal of the driving element from the recess.

9. The endcap of claim 1, wherein the elastic tabs are configured to frictionally engage an exterior surface of the driving element received therein.

10. The endcap of claim 1, wherein the elastic tabs are configured to lockingly engage a groove of the driving element received therein.

11. The endcap of claim 1, wherein the recess has a substantially polygonal cross-section.

12. The endcap of claim 1, wherein the recess has a substantially hexagonal cross-section.

13. The endcap of claim 1, wherein the endcap further includes a lumen extending longitudinally therethrough, the lumen sized and shaped to receive a guidewire therethrough.

14. A system for engaging a proximal end of an intramedullary nail, comprising:
    (i) a tool comprising a drive shaft having a driving element; and
    (ii) an endcap comprising:
        a body extending from a first end to a second end and configured to engage a channel of an intramedullary nail, and
        a head portion at the first end of the body, the head portion including a recess sized and shaped to receive the driving element of the drive shaft, the recess including elastic tabs biased to extend radially toward a central axis of the recess to engage and retain the driving element therein.

15. The system of claim 14, wherein the driving element has a concave exterior shape.

16. The system of claim 15, wherein the driving element tapers from a midpoint to a narrower proximal end, and tapers from the midpoint to a narrower distal end.

17. The system of claim 14, further comprising a guidewire slidably inserted through the endcap to align the driving element to engage the head portion of the endcap, wherein the endcap includes a lumen extending longitudinally therethrough, the lumen sized and shaped to receive the guidewire therethrough.

18. The system of claim 17, wherein the recess has a correspondingly polygonal shape to the substantially polygonal cross-section of the driving element to lockingly engage the driving element therein.

19. The system of claim 14, wherein the driving element has a substantially polygonal cross-section.

* * * * *